US011744782B2

(12) United States Patent
Mitamura et al.

(10) Patent No.: US 11,744,782 B2
(45) Date of Patent: Sep. 5, 2023

(54) SEPARATELY PACKED CURABLE COMPOSITION

(71) Applicant: MITSUI CHEMICALS, INC., Tokyo (JP)

(72) Inventors: Takenori Mitamura, Ichihara (JP); Yoko Kosugi, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 706 days.

(21) Appl. No.: 16/634,017

(22) PCT Filed: Aug. 7, 2018

(86) PCT No.: PCT/JP2018/029561
§ 371 (c)(1),
(2) Date: Jan. 24, 2020

(87) PCT Pub. No.: WO2019/031488
PCT Pub. Date: Feb. 14, 2019

(65) Prior Publication Data
US 2021/0169749 A1 Jun. 10, 2021

(30) Foreign Application Priority Data
Aug. 7, 2017 (JP) ................................. 2017-152436

(51) Int. Cl.
| *A61K 6/893* | (2020.01) |
| *A61K 6/30* | (2020.01) |
| *A61K 6/20* | (2020.01) |
| *A61K 6/887* | (2020.01) |
| *A61K 6/86* | (2020.01) |
| *A61K 6/836* | (2020.01) |
| *A61K 6/891* | (2020.01) |
| *A61K 6/62* | (2020.01) |
| *A61K 6/84* | (2020.01) |
| *C08F 222/38* | (2006.01) |

(52) U.S. Cl.
CPC ................ *A61K 6/893* (2020.01); *A61K 6/20* (2020.01); *A61K 6/30* (2020.01); *A61K 6/62* (2020.01); *A61K 6/836* (2020.01); *A61K 6/84* (2020.01); *A61K 6/86* (2020.01); *A61K 6/887* (2020.01); *A61K 6/891* (2020.01); *C08F 222/38* (2013.01)

(58) Field of Classification Search
CPC ...................................................... A61K 6/893
See application file for complete search history.

(56) References Cited

U.S. PATENT DOCUMENTS

| 8,297,975 | B2 | 10/2012 | Yamamoto et al. |
| 8,545,225 | B2 | 10/2013 | Takei et al. |
| 9,511,004 | B2 | 12/2016 | Naruse et al. |
| 10,022,307 | B2 | 7/2018 | Chisholm et al. |
| 10,478,385 | B2 | 11/2019 | Suzuki |
| 2007/0040151 | A1 | 2/2007 | Utterodt et al. |
| 2010/0292359 | A1 | 11/2010 | Yamamoto et al. |
| 2010/0311864 | A1 | 12/2010 | Arita et al. |
| 2012/0016094 | A1 | 1/2012 | Takei et al. |
| 2012/0296003 | A1 | 11/2012 | Naruse et al. |
| 2015/0051603 | A1 | 2/2015 | Chisholm et al. |
| 2016/0175805 | A1 | 6/2016 | Catchpole et al. |
| 2016/0184143 | A1 | 6/2016 | Hooi |
| 2019/0000722 | A1 | 1/2019 | Suzuki |

FOREIGN PATENT DOCUMENTS

| EP | 2 156 817 A1 | 2/2010 |
| JP | 3449843 B2 | 9/2003 |
| JP | 2009-167132 A | 7/2009 |
| JP | 2010-280630 A | 12/2010 |
| JP | 2011-016776 A | 1/2011 |
| JP | 2011-063537 A | 3/2011 |
| JP | 2012-131717 A | 7/2012 |
| JP | 2012131717 A * | 7/2012 |
| JP | 5191486 B2 | 5/2013 |
| JP | 2014-214122 A | 11/2014 |
| JP | 2014214122 A * | 11/2014 |
| JP | 2015-517004 A | 6/2015 |
| JP | 5773557 B2 | 9/2015 |
| JP | 5878065 B2 | 3/2016 |
| JP | 2016-094482 A | 5/2016 |
| WO | 2008/140103 A1 | 11/2008 |
| WO | 2012/157566 A1 | 11/2012 |
| WO | 2013/046648 A1 | 4/2013 |
| WO | 2013/144590 A1 | 10/2013 |

(Continued)

OTHER PUBLICATIONS

Extended European Search Report dated Nov. 13, 2020, issued by the European Patent Office in corresponding European Application No. 18843972.3-1103, (10 pages).

Notice of Reasons for Refusal dated Oct. 20, 2020, by the Japanese Patent Office in corresponding Japanese Patent Application No. 2019-535666 and an English translation of the Notice. (10 pages).

(Continued)

*Primary Examiner* — Benjamin J Packard

(74) *Attorney, Agent, or Firm* — Buchanan Ingersoll & Rooney PC

(57) ABSTRACT

Provided is a curable composition that has a sufficient pot life and does not cause a significant delay in curing time even after long-term storage at room temperature or higher. A separately packed curable composition includes: (A) a first pack containing: (a1) a polymerizable monomer having no acidic group, (b) a polymerizable monomer having an acidic group, and (c) a transition metal compound; and (B) a second pack containing: (a2) a polymerizable monomer having no acidic group, (d) an aromatic amine compound, and (e) at least one compound selected from sulfinic acid and a salt thereof.

14 Claims, No Drawings

(56) References Cited

FOREIGN PATENT DOCUMENTS

| WO | 2015/015220 A1 | 2/2015 |
| WO | 2015/015221 A1 | 2/2015 |
| WO | 2017/104128 A1 | 6/2017 |

OTHER PUBLICATIONS

International Search Report (PCT/ISA/210) and Written Opinion (PCT/ISA/237) dated Sep. 18, 2018, by the Japanese Patent Office in corresponding International Patent Application No. PCT/JP2018/029561 and English translations thereof. (14 pages).

\* cited by examiner

SEPARATELY PACKED CURABLE COMPOSITION

TECHNICAL FIELD

The present invention relates to a separately packed curable composition.

BACKGROUND ART

Various restorative materials are being used nowadays in dental treatment, and materials classified as organic restorative materials are practically used, including dental adhesive resin cements, dental self-adhesive composite resins, dental adhesives, and dental backing layers, dental root fillers, orthodontic adhesives, mobile tooth fixing materials, tooth fissure sealants (dental sealants), and dental root-temperature polymerization resins. For such dental curable compositions, a curable composition including a polymerizable monomer capable of radical polymerization and a radical polymerization initiator is widely used.

The main types of radical polymerization initiators contained in dental curable compositions are photopolymerization initiators, which achieves polymerization and curing through irradiation with visible light, and chemical polymerization initiators, which achieves polymerization and curing by mixing two or more separately stored packs immediately before use. Dual-cure type products that include both of those types of initiators are also widely used nowadays in dental practice.

Among radical polymerization initiators, photopolymerization initiators are characterized by providing a comparatively low level of polymerization inhibition due to oxygen in the course of polymerization, and can easily obtain a high polymerization rate by visible light irradiation in a short time. On the other hand, since photopolymerization initiators are not suited to parts where it is difficult for the light from the irradiation device to reach, such as a part hiding behind a cavity or a part where the treatment site is deep in the tooth. For these cases, dental curable compositions containing a chemical polymerization initiator are mainly used.

One common chemical polymerization initiator system is a redox type polymerization initiator that combines an oxidizing agent and a reducing agent. A curable composition containing a redox polymerization initiator is usually stored in the form of a separately packed curable composition that is divided into the first pack including an oxidizing agent and the second pack including a reducing agent until immediately before use. When the first pack including the oxidizing agent and the second pack including the reducing agent are mixed, a redox reaction occurs to generate radicals, which react with a polymerizable monomer to initiate a polymerization reaction, and curing of the mixture thus progresses. Therefore, an oxidizing agent and a reducing agent that can cause a redox reaction cannot usually be blended or stored together in the same pack. In order to maintain the activity of the chemical polymerization initiator when mixed, the separately packed curable composition needs to be divided into three or more packs in some cases.

As a chemical polymerizable, separately packed curable composition, there is known a separately packed dental composition including a first pack that includes benzoyl peroxide as an oxidizing agent, a second pack that includes an amine compound as a reducing agent, and optionally a sulfinic acid compound as a polymerization accelerator (e.g., see Patent Literature 1). From this separately packed curable composition, a mixture having sufficient curability even in the oral cavity can be prepared, and hence such a separately packed curable composition has been conventionally used. However, curable compositions that include benzoyl peroxide often have low storage stability due to the thermal stability of benzoyl peroxide, and in many cases suffer from handling problems, such as requiring refrigeration. Furthermore, if the amount of benzoyl peroxide blended is reduced in order to secure a longer pot life, it may no longer be possible to obtain a mixture having sufficient polymerization properties. On the other hand, if a polymerizable monomer is included with an increased amount of benzoyl peroxide in the first pack of the separately packed curable composition in order to ensure long-term storage stability, the composition may undergo curing during storage, depending on the storage conditions, for example, during storage at comparatively high temperature, which makes it difficult to cope with a long storage period.

Therefore, as a separately packed curable composition that solves the above problems, there has been proposed a separately packed curable composition that includes a first pack including, in addition to benzoyl peroxide, another peroxide such as hydroperoxide or peroxyester, and a second pack including an aromatic amine (e.g., see Patent Literature 2). This separately packed curable composition, which includes a thermally stable peroxide in the first pack, is characterized by having better storage stability than a composition including a first pack using benzoyl peroxide alone. However, although the polymerization properties of the mixture prepared from this separately packed curable composition are maintained, a delay occurs in the curing time over time, if the separately packed curable composition is stored in an environment at room temperature or higher, and hence there is room for improvement.

Patent Literature 3 proposes using a second pack that includes a salt of an aromatic amine compound as an active species of a reducing agent in order to enable long-term storage of a separately packed curable composition. However, because a first pack including benzoyl peroxide as an oxidizing agent is used, it is necessary to store at a low temperature, in order to maintain the polymerization properties of the mixture produced from the separately packed curable composition, and hence there is room for improvement. Further, Patent Literature 4 proposes a separately packed curable composition that includes a first pack including cumene hydroperoxide and a second pack including a thiourea derivative represented by N-acetylthiourea and a copper compound as an accelerator.

This separately packed curable composition has a comparatively high stability to heat, and the mixture of the first pack and the second pack exhibits comparatively good polymerization curability. However, the chemical polymerization catalyst system of Patent Literature 4 still has a lower polymerization reactivity than the conventional chemical polymerization catalyst system composed of benzoyl peroxide/aromatic amine. In addition, the pot life after the storage of the separately packed curable composition changes greatly over time, and the mixture obtained by mixing the first pack and the second pack after storage tends to solidify, which are problematic.

Further, in Patent Literatures 1, 3, and 4, the separately packed curable compositions include a peroxide and a reducing agent such as an amine compound to be mixed together to form a component serving as a chemical polymerization initiator, and also include, as a component thereof, a polymerizable monomer including an acidic group for the purpose of imparting adhesive properties. In many separately packed curable compositions like those in these Patent Literatures, the peroxide and the polymerizable monomer including an acidic group are included in the same pack for the storage stability of the reducing agent. This can be one of the factors of a deterioration of the polymerization properties occurring in the pack during storage, since peroxides tend to decompose in an acidic atmosphere.

CITATION LIST

Patent Literature

Patent Literature 1: Japanese Patent No. 3449843
Patent Literature 2: Japanese Patent No. 5878065
Patent Literature 3: Japanese Patent No. 5191486
Patent Literature 4: Japanese Patent No. 5773557

SUMMARY OF INVENTION

Technical Problem

It is desired that a dental curable composition used as a dental material have excellent adhesion strength to dentine. In order to exhibit this performance, it is desired that the dental curable composition be curable by polymerization even in an oral cavity and under acidic conditions. More specifically, it is desired that the dental curable composition have a reasonably high curing rate and a reasonably long pot life in practical use. Further, it is desired that the dental curable composition have a sufficient polymerization activity and have little variation in curing time even when stored for a long period of time.

It is an object of the present invention to provide a curable composition that has a sufficient pot life and does not cause a significant delay in curing time even after long-term storage at room temperature or higher.

Solution to Problem

As a result of intensive studies to solve the above-mentioned problems, the present inventors have found that those problems can be solved by appropriately and separately packaging a chemical polymerization initiator comprising a vanadium compound, an aromatic amine compound, and at least one compound selected from sulfinic acid and a salt thereof in a curable composition comprising a polymerizable monomer having an acidic group and a polymerizable monomer not containing an acidic group as its components, and thus have completed the present invention.

The present invention includes the matters described in the following [1] to [15]

[1] A separately packed curable composition, including:
  (A) a first pack containing:
    (a1) a polymerizable monomer having no acidic group,
    (b) a polymerizable monomer having an acidic group, and
    (c) a transition metal compound; and
  (B) a second pack containing:
    (a2) a polymerizable monomer having no acidic group,
    (d) an aromatic amine compound, and
    (e) at least one compound selected from sulfinic acid and a salt thereof.

[2] The separately packed curable composition according to [1], wherein the metal constituting the transition metal compound (c) is an early transition metal.

[3] The separately packed curable composition according to [1] or [2], wherein the transition metal compound (c) is a vanadium compound.

[4] The separately packed curable composition according to any of [1] to [3], wherein the second pack (B) contains a peroxyester compound (fa) and/or an alkyl peroxide (fb).

[5] The separately packed curable composition according to any of [1] to [4], wherein the second pack (B) contains a photopolymerization initiator (g).

[6] The separately packed curable composition according to any of [1] to [5], wherein at least one of the first pack (A) and the second pack (B) contains a filler (h).

[7] The separately packed curable composition according to any of [1] to [6], wherein a total of the transition metal compound (c), the aromatic amine (d), and the at least one compound (e) selected from sulfinic acid and a salt thereof is 0.02 to 30 parts by mass based on 100 parts by mass of a total of the polymerizable monomers (a1) and (a2) having no acidic group and the polymerizable monomer (b) having an acidic group that are included in the first pack (A) and the second pack (B).

[8] The separately packed curable composition according to any of [1] to [7], wherein a content of the transition metal compound (c) in the first pack (A) is 0.001 to 5 parts by mass based on 100 parts by mass of a total of the polymerizable monomers (a1) and (a2) having no acidic group and the polymerizable monomer (b) having an acidic group that are included in the first pack (A) and the second pack (B).

[9] The separately packed curable composition according to any of [1] to [8], wherein a content of the aromatic amine (d) in the second pack (B) is 0.01 to 5 parts by mass based on 100 parts by mass of a total of the polymerizable monomers (a1) and (a2) having no acidic group and the polymerizable monomer (b) having an acidic group that are included in the first pack (A) and the second pack (B).

[10] The separately packed curable composition according to any of [1] to [9], wherein a content of the at least one compound (e) selected from sulfinic acid and a salt thereof in the second pack (B) is 0.01 to 20 parts by mass based on 100 parts by mass of a total of the polymerizable monomers (a1) and (a2) having no acidic group and the polymerizable monomer (b) having an acidic group that are included in the first pack (A) and the second pack (B).

[11] A cured product of a mixture including the first pack (A) and the second pack (B) of the separately packed curable composition according to any of [1] to [10].

[12] A dental material including the separately packed curable composition according to any of [1] to [10].

[13] The dental material according to [12], wherein the dental material is one dental material selected from the group consisting of a dental adhesive resin cement, a dental composite resin, a dental backing material, a dental root filler, an orthodontic adhesive, a mobile tooth fixing material, and a dental sealant.

[14] A polymerization initiator kit, including:
  a first member including:
    (c) a transition metal compound; and
  a second member including:
    (d) an aromatic amine compound and
    (e) at least one compound selected from sulfinic acid and a salt thereof, the aromatic amine compound (d) and the at least one compound (e) being accommodated together or separately.

[15] A curable composition kit, including:
a first member including:
(c) a transition metal compound; and
a second member including:
(d) an aromatic amine compound and
(e) at least one compound selected from sulfinic acid and a salt thereof,
the aromatic amine compound (d) and the at least one compound (e) being accommodated together or separately,
wherein at least one polymerizable monomer is included in either one of the first member or the second member, or included in another member other than the first member and the second member.

Advantageous Effects of Invention

The separately packed curable composition of the present invention has a sufficient pot life without causing a significant delay in curing time and also maintain sufficient polymerization activity, in a mixture prepared from the separately packed composition even after long-term storage at room temperature or higher.

DESCRIPTION OF EMBODIMENTS

The present invention will now be described in detail. Herein, "(meth)acryl" means acryl or methacryl, and for example, "(meth)acrylic acid" means acrylic acid or methacrylic acid. Similarly, "(meth)acryloyl" means "acryloyl" or "methacryloyl", and "(meth)acrylate" means "acrylate" or "methacrylate".

The separately packed curable composition of the present invention contains the following first pack (A) and the following second pack (B) separately.

(First Pack (A))

The first pack (A) contains: (a1) a polymerizable monomer having no acidic group; (b) a polymerizable monomer having an acidic group; and (c) a transition metal compound.

((a1) Polymerizable Monomer Having No Acidic Group)

Because of including the polymerizable monomer (a1) having no acidic group in the curable composition, various physical properties of the obtained cured product, such as mechanical strength and adhesive strength, can be improved. Moreover, because the first pack (A) contains the polymerizable monomer (a1) having no acidic group, the fluidity of the first pack (A) can be improved.

Examples of the polymerizable monomer (a1) having no acidic group include a radical polymerizable monomer having no acidic group. Examples of a radical polymerizable unsaturated group included in the radical polymerizable monomer having no acidic group include a (meth)acryloyl group, a (meth)acrylamide group, a styryl group, a vinyl group, and an allyl group. Among these radically polymerizable unsaturated groups, in view of ease of removal of the polymerizable group by hydrolysis in the oral cavity, for example, a (meth)acryloyl group and a (meth)acrylamide group are preferred, a methacryloyl group and a (meth)acrylamide group are more preferred, and a methacryloyl group is still more preferred.

Examples of the radical polymerizable monomer having no acidic group include:
hydroxyalkyl (meth)acrylates, such as 2-hydroxyethyl (meth)acrylate, 3-hydroxypropyl (meth)acrylate, 4-hydroxybutyl (meth)acrylate, 6-hydroxyhexyl (meth)acrylate, and 10-hydroxydecyl (meth)acrylate;

monofunctional monomers, such as 2-(dimethylamino) ethyl methacrylate, N-methyl-N-phenylaminoethyl (meth)acrylate, N-ethyl-N-phenylaminoethyl (meth)acrylate, propylene glycol mono(meth)acrylate, glycerol mono(meth)acrylate, erythritol mono(meth)acrylate, N-methylol (meth)acrylamide, N-hydroxyethyl (meth)acrylamide, N,N-(dihydroxyethyl) (meth)acrylamide, methyl (meth)acrylate, ethyl (meth)acrylate, propyl (meth)acrylate, isopropyl (meth)acrylate, butyl (meth)acrylate, isobutyl (meth)acrylate, benzyl (meth)acrylate, lauryl (meth)acrylate, 2,3-dibromopropyl (meth)acrylate, 3-(meth)acryloyloxypropyltrimethoxysilane, 11-(meth)acryloyloxyundecyltrimethoxysilane, (meth)acrylamide, dimethylaminoethyl (meth)acrylate, dimethylaminopropyl (meth)acrylate, dimethylaminobutyl (meth)acrylate, (meth)acryloyloxy dodecylpyridinium bromide, (meth)acryloyloxy dodecylpyridinium chloride, and (meth)acryloyloxy hexadecylpyridinium chloride;

bifunctional monomers having an aromatic ring, such as 2,2-bis((meth)acryloyloxyphenyl) propane, 2,2-bis[4-(3-(meth)acryloyloxy-2-hydroxypropoxy)phenyl] propane (commonly referred to as "Bis-GMA"), 2,2-bis(4-(meth)acryloyloxyphenyl) propane, 2,2-bis(4-(meth)acryloyloxypolyethoxyphenyl) propane, 2,2-bis(4-(meth)acryloyloxydiethoxy)phenyl) propane), 2,2-bis(4-(meth)acryloyloxytetraethoxyphenyl) propane, 2,2-bis(4-(meth)acryloyloxypentaethoxyphenyl) propane, 2,2-bis(4-(meth)acryloyloxydipropoxyphenyl) propane, 2-(4-(meth)acryloyloxyethoxyphenyl)-2-(4-(meth)acryloyloxydiethoxyphenyl) propane, 2-(4-(meth)acryloyloxydiethoxyphenyl)-2-(4-(meth)acryloyloxytriethoxyphenyl) propane, 2-(4-(meth)acryloyloxydipropoxyphenyl)-2-(4-(meth)acryloyloxytriethoxyphenyl) propane, 2,2-bis(4-(meth)acryloyloxypropoxyphenyl) propane, 2,2-bis(4-(meth)acryloyloxyisopropoxyphenyl) propane, and 1,4-bis(2-(meth)acryloyloxyethyl) pyromellitate;

bifunctional monomers having an aliphatic carbon chain, such as alkylene glycol di(meth)acrylates such as glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, and neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,12-dodecanediol di(meth)acrylate, 1,2-bis(3-(meth)acryloyloxy-2-hydroxypropoxy) ethane, 2,2,4-trimethylhexamethylene bis(2-carbamoyloxyethyl) dimethacrylate (commonly referred to as "UDMA"), and 1,2-bis(3-(meth)acryloyloxy-2-hydroxypropoxy) ethane;

trifunctional or higher polyfunctional monomers, such as trimethylolpropane tri(meth)acrylate, trimethylolethane tri(meth)acrylate, trimethylolmethane tri(meth)acrylate, tris(2-(meth)acryloxyethyl) isocyanurate, pentaerythritol tri(meth)acrylate, pentaerythritol tetra(meth)acrylate, dipentaerythritol penta(meth)acrylate, N,N-(2,2,4-trimethylhexamethylene) bis[2-(aminocarboxy)propane-1,3-diol]tetramethacrylate, and 1,7-diacryloyloxy-2,2,6,6-tetraacryloyloxymethyl-4-oxyheptane;

compounds having an isocyanate group (—NCO), such as hexamethylene diisocyanate (HDI), tolylene diisocyanate (TDI), xylylene diisocyanate (XDI), diphenylmethane diisocyanate (MDI), isophorone diisocyanate (IPDI), and trimethylhexamethylene diisocyanate (TMHMDI);

polymerizable monomers synthesized by an addition reaction with a (meth)acrylate compound having a hydroxyl group (—OH) (e.g., described in International Publication No. 2012/157566, International Publication No. 2015/015220, International Publication No. 2015/015221, and Japanese Patent Application Laid-open No. 2016-094482), such as 2-hydroxyethyl (meth)acrylate, 2-hydroxypropyl (meth)acrylate, 2-hydroxybutyl (meth)acrylate, 6-hydroxyhexyl (meth)acrylate, 10-hydroxydecyl (meth)acrylate, 3-chloro-2-hydroxypropyl (meth)acrylate, 2-hydroxy-3-phenoxypropyl (meth)acrylate, glycerin mono(meth)acrylate, N-hydroxyethyl (meth)acrylamide, N,N-(dihydroxyethyl) (meth)acrylamide, bisphenol A diglycidyl (meth)acrylate, 2-hydroxy-3-acryloyloxypropyl (meth)acrylate, 2,2-bis[4-[3-(meth)acryloyloxy-2-hydroxypropoxy]phenyl] propane, 1,2-bis[3-(meth)acryloyloxy-2-hydroxypropoxy]ethane, pentaerythritol tri (meth)acrylate, and dipentaerythril tri- or tetra-(meth)acrylate.

Among the radical polymerizable monomers having no acidic group, 2,2,4-trimethylhexamethylene bis(2-carbamoyloxyethyl) dimethacrylate (UDMA), bisphenol A diglycidyl methacrylate (Bis-GMA), and 2,2-bis (4-methacryloyloxypolyethoxyphenyl) propane, a compound having an average addition mole number of ethoxy groups of 2.6 (commonly referred to as "D-2.6E")), 2-hydroxyethyl methacrylate (HEMA), and triethylene glycol dimethacrylate (TEGDMA) are preferred in view of physical properties and ease of handling.

These compounds as the polymerizable monomer (a1) having no acidic group may be used singly or in combination of two or more thereof.

The content of the polymerizable monomer (a1) having no acidic group in the first pack (A) is preferably 20 to 98 parts by mass, more preferably 50 to 94 parts by mass, and further preferably 70 to 90 parts by mass, based on 100 parts by mass of a total of the polymerizable monomer (a1) having no acidic group of the first pack (A) and the polymerizable monomer (b) (described later) having an acidic group that are included in the separately packed curable composition. By setting the content of the polymerizable monomer (a1) having no acidic group in the first pack (A) in the above range, the fluidity of the first pack (A) can be improved, and the mechanical strength and adhesive strength of the cured product obtained from the mixture of the first pack (A) and the second pack (B) can be improved.

((b) Polymerizable Monomer Having an Acidic Group)

Because of the polymerizable monomer (b) having an acidic group in the separately packed curable composition of the present invention, a curable composition having excellent adhesion can be obtained. Moreover, because of including the polymerizable monomer (b) having an acidic group in the first pack (A), performance is not impaired during storage.

Examples of the polymerizable monomer (b) having an acidic group include an acidic group-containing radical polymerizable monomer. A conventionally used polymerizable monomer can be used as a dental adhesive monomer. Examples of the acidic group included in the polymerizable monomer (b) having an acidic group include a carboxylic acid group, a carboxylic anhydride group, a phosphoric acid group, a thiophosphoric acid group, a pyrophosphoric acid group, a thiopyrophosphoric acid group, a phosphonic acid group, a thiophosphonic acid group, a sulfonic acid group, and the like. These acidic groups may be in the form of an acid chloride, an alkali metal salt, an alkaline earth metal salt, an ammonium salts, and the like.

Examples of the polymerizable monomer having a phosphoric acid group include (meth)acryloyloxy alkyl dihydrogen phosphates, such as 2-(meth)acryloyloxy ethyl dihydrogen phosphate, 3-(meth)acryloyloxy propyl dihydrogen phosphate, 4-(meth)acryloyloxy butyl dihydrogen phosphate, 5-(meth)acryloyloxy pentyl dihydrogen phosphate, 6-(meth)acryloyloxy hexyl dihydrogen phosphate, 7-(meth) acryloyloxy heptyl dihydrogen phosphate, 8-(meth)acryloyloxy octyl dihydrogen phosphate, 9-(meth)acryloyloxy nonyl dihydrogen phosphate, 10-(meth)acryloyloxy decyl dihydrogen phosphate, 11-(meth)acryloyloxy undecyl dihydrogen phosphate, 12-(meth)acryloyloxy dodecyl dihydrogen phosphate, 16-(meth)acryloyloxy hexadecyl dihydrogen phosphate, and 20-(meth)acryloyloxy icosyl dihydrogen phosphate, bis[(meth)acryloyloxyalkyl] hydrogen phosphates, such as bis[2-(meth)acryloyloxyethyl] hydrogen phosphate, bis[4-(meth)acryloyloxybutyl] hydrogen phosphate, bis[6-(meth)acryloyloxyhexyl] hydrogen phosphate, bis[8-((meth)acryloyloxyoctyl] hydrogen phosphate, bis[9-(meth)acryloyloxynonyl] hydrogen phosphate, and bis[10-(meth)acryloyloxydecyl] hydrogen phosphate, 1,3-di(meth)acryloyloxypropyl dihydrogen phosphate, 2-(meth)acryloyloxyethyl phenyl hydrogen phosphate, 2-(meth)acryloyloxyethyl-2-bromoethyl hydrogen phosphate, bis[2-(meth)acryloyloxy-(1-hydroxymethyl)ethyl] hydrogen phosphate, pentaacryloyl dipentaerythritol hydrogen phosphate, and acid chlorides, alkali metal salts, alkaline earth metal salts, ammonium salts, and the like thereof. Further examples include compounds in which the phosphate acid group in these compounds is substituted with a thiophosphoric acid group.

Examples of the polymerizable monomer having a pyrophosphate acid group include bis[2-(meth)acryloyloxyethyl] pyrophosphate, bis[4-(meth)acryloyloxybutyl] pyrophosphate, bis[6-(meth)acryloyloxyhexyl] pyrophosphate, bis[8-(meth)acryloyloxyoctyl] pyrophosphate, bis[10-(meth)acryloyloxydecyl] pyrophosphate, and acid chlorides, alkali metal salts, alkaline earth metals salts, ammonium salts, and the like thereof. Further examples include compounds in which the pyrophosphate acid group in these compounds is substituted with a thiopyrophosphate acid group.

Examples of the polymerizable monomer having a phosphonic acid group include 2-(meth)acryloyloxyethyl phenylphosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, 10-(meth)acryloyloxydecyl-3-phosphonoacetate, and acid chlorides, alkali metal salts, alkaline earth metal salts, ammonium salts, and the like thereof. Further examples include compounds in which the phosphonic acid group in these compounds is substituted with a thiophosphonic acid group.

Examples of the polymerizable monomer having a sulfonic acid group include 2-sulfoethyl (meth)acrylate, 2-sulfo-1-propyl (meth)acrylate, 1-sulfo-2-propyl (meth)acrylate, 1-sulfo-2-butyl (meth)acrylate, 3-sulfo-2-butyl (meth)acrylate, 3-bromo-2-sulfo-2-propyl (meth)acrylate, 3-methoxy-1-sulfo-2-propyl (meth)acrylate, 1,1-dimethyl-2-sulfoethyl (meth)acrylamide, and acid chlorides, alkali metal salts, alkaline earth metal salts, and ammonium salts thereof.

Examples of the polymerizable monomer having a carboxylic acid group or a carboxylic acid anhydride group include monocarboxylic acids, dicarboxylic acids, tricarboxylic acids, and tetracarboxylic acids, or derivatives thereof. Examples of these include (meth)acrylic acid, maleic acid, p-vinylbenzoic acid, 11-(meth)acryloyloxy-1,1-undecanedicarboxylic acid (in the case of methacrylate: "MAC10"), 1,4-di(meth)acryloyloxy ethyl pyromellitic acid, 6-(meth)acryloyloxyethylnaphthalene-1,2,6-tricarboxylic acid, 4-(meth)acryloyloxymethyl trimellitic acid and anhydrides thereof, 4-(meth)acryloyloxyethyl trimellitic acid (in the case of methacrylate: "4-MET") and anhydrides thereof (in the case of methacrylate: 4-META), 4-(meth)acryloyloxybutyl trimellitic acid and anhydrides thereof, 4-[2-hydroxy-3-(meth)acryloyloxy] butyl trimellitic acid and anhydrides thereof, 2,3-bis(3,4-dicarboxybenzoyloxy) propyl (meth)acrylate, N,O-di(meth)acryloyl tyrosine, O-(meth)acryloyl tyrosine, N-(meth)acryloyl tyrosine, N-(meth)acryloylphenylalanine, N-(meth)acryloyl-p-aminobenzoic acid, N-(meth)acryloyl-O-aminobenzoic acid, N-(meth)acryloyl-5-aminosalicylic acid (in the case of methacrylate: "5-MASA"), N-(meth)acryloyl-4-aminosalicylic acid, 2 or 3 or 4-(meth)acryloyloxybenzoic acid, an addition product of 2-hydroxyethyl (meth)acrylate and pyromellitic acid dianhydride (in the case of methacrylate: "PMDM"), an addition reaction product of 2-hydroxyethyl (meth)acrylate and maleic anhydride or 3,3',4,4'-benzophenonetetracarboxylic dianhydride (in the case of methacrylate: "BTDA") or 3,3',4,4'-biphenyltetracarboxylic dianhydride, 2-(3,4-dicarboxybenzoyloxy)-1,3-di(meth)acryloyloxypropane, an adduct of N-phenylglycine or N-tolylglycine and glycidyl (meth)acrylate, 4-[(2-hydroxy-3-(meth)acryloyloxypropyl)amino] phthalic acid, 3 or 4-[N-methyl-N-(2-hydroxy-3-(meth)acryloyloxypropyl)amino] phthalic acid, and acid chlorides, alkali metal salts, alkaline earth metal salts, ammonium salts, and the like thereof.

Among the above-mentioned monomers (b) having an acidic group, 4-methacryloxyethyl trimellitic acid, 4-methacryloxyethyl trimellitic anhydride, and 10-methacryloxydecylhydrogen phosphate are preferred in view of adhesion to teeth.

These compound as the polymerizable monomer (b) having an acidic group may be used singly or in combination of two or more thereof.

The content of the polymerizable monomer (b) having an acidic group is preferably 1 to 40 parts by mass, more preferably 3 to 25 parts by mass, and further preferably 5 to 15 parts by mass, based on 100 parts by mass of a total of the polymerizable monomers (a1) and (a2) having no acidic group and the polymerizable monomer (b) having an acidic group that are included in the first pack (A) and the second pack (B). If the content of the polymerizable monomer (b) having an acidic group is within the above range, the mixture obtained by mixing the first pack (A) and the second pack (B) has excellent polymerization properties, and the cured product to be obtained tends to have excellent adhesive strength.

((c) Transition Metal Compound)

Because of including the transition metal compound (c) in the separately packed curable composition of the present invention, the curable composition can be cured while securing a sufficient pot life. Further, because of including the transition metal compound (c) in the first pack (A), there is no adverse effect on the components included in the second pack (B) during storage. Examples of the transition metal compound (c) include vanadium compounds, copper compounds, and molybdenum compounds.

The vanadium compound is preferably at least one compound selected from trivalent to pentavalent vanadium compounds, such as vanadium(III) acetylacetonate, vanadium (III) naphthenate, vanadyl stearate, vanadium benzoylacetonate, bis(maltolate) oxovanadium(IV), oxobis(1-phenyl-1,3-butanedione) vanadium(IV), vanadyl(IV) acetylacetonate, divanadium(IV) tetroxide, vanadyl(IV) oxalate, vanadyl(IV) sulfate, oxobis(1-phenyl-1,3-butanedionate) vanadium(IV), bis(maltolate) oxovanadium(IV), vanadium(V) oxytriisopropoxide, vanadium(V) pentoxide, sodium metavanadate(V), ammonium metavanadate (V), and the like.

Examples of the copper compound include monovalent to divalent copper compounds, such as copper acetylacetonate, copper oleate, copper acetate, copper gluconate, copper citrate, copper phthalate, copper naphthenate, copper hydroxide, copper methoxide, copper ethoxide, copper isopropoxide, copper chloride, and copper bromide.

Examples of the molybdenum compound include molybdenum(IV) oxide, molybdenum oxide acetylacetonate, molybdenium ethoxide, bis(2,4-pentadionato) molybdenium oxide, molybdenyl diethyldithiocarbamate, and the like.

In the present invention, when the curable composition is used for dental use, discoloration of the cured product becomes an issue. In view of further suppressing the discoloration, it is preferred that the transition metal constituting the transition metal compound (c) be an early transition metal. The early transition metal refers to a transition metal having an element number in groups 3 to 7 in the periodic table. Among these, period 4 transition metals are preferred in view of obtaining sufficient polymerization activity and excellent storage stability. Among the early transition metals, the fourth period transition metals are, specifically, scandium, titanium, vanadium, chromium, and manganese.

Among these transition metal compounds (c), vanadium compounds are preferred in view of the polymerization properties of the mixture prepared from the first pack (A) and the second pack (B), the aesthetics when used in the oral cavity, and the capability of suppressing discoloration. Moreover, in view of solubility in a polymerizable monomer and handling, vanadium(III) acetylacetonate and vanadyl (IV) acetylacetonate are preferred.

These compounds as the transition metal compound (c) may be used singly or in combination of two or more thereof.

The content of the transition metal compound (c) is preferably 0.001 to 5 parts by mass, more preferably 0.005 to 3 parts by mass, and further preferably 0.01 to 1 part by mass, based on 100 parts by mass of a total of the polymerizable monomers (a1) and (a2) having no acidic group, and the polymerizable monomer (b) having an acidic group included in the first pack (A) and the second pack (B). If the content of the transition metal compound (c) is less than this lower limit, the effects brought about by the inclusion of the transition metal compound (c) may not be obtained, and if the content is more than this upper limit, the polymerizable monomer included in the first pack (A) tends to be more easily polymerized during storage.

(Second Pack (B))

The second pack (B) included in the separately packed curable composition of the present invention contains: (a2) a polymerizable monomer having no acidic group, (d) an aromatic amine compound, and (e) at least one compound selected from sulfinic acid and a salt thereof.

((a2) Polymerizable Monomer Having No Acidic Group)

In addition, since the second pack (B) contains the polymerizable monomer (a2) having no acidic group, the fluidity and ease of handling of the second pack (B) can be improved, and the mechanical strength and adhesive strength of the cured product obtained from the mixture of the first pack (A) and the second pack (B) can be improved.

The details of the polymerizable monomer (a2) having no acidic group, such as specific examples and preferred examples thereof, are the same as those described for the polymerizable monomer (a1) having no acidic group included in the first pack (A).

The content of the polymerizable monomers (a1) and (a2) having no acidic group is preferably 60 to 99 parts by mass, more preferably 75 to 97 parts by mass, and further preferably 85 to 95 parts by mass, based on 100 parts by mass of a total of the polymerizable monomers (a1) and (a2) having no acidic group and the polymerizable monomer (b) having an acidic group that are included in the first pack (A) and the second pack (B) of the separately packed curable composition. By setting the content of the polymerizable monomers having no acidic group in the above range, the cured product obtained from the mixture of the first pack (A) and the second pack (B) tends to have excellent mechanical strength and adhesive strength.

((d) Aromatic Amine Compound)

Because of including the aromatic amine compound (d) in the separately packed curable composition of the present invention, the aromatic amine compound (d) acts as a polymerization initiator or as one component promoting polymerization. In addition, because of including the aromatic amine compound (d) in the second pack (B), performance is not impaired during storage.

The aromatic amine compound (d) is a compound that includes one or more aromatic rings having a moiety formed by bonding a nitrogen atom and an unsaturated hydrocarbon. Such aromatic amine compounds also include amino acid compounds or salts thereof. Examples of the aromatic ring include a phenyl ring and a naphthyl ring. As the aromatic amine compound (d), a compound including one aromatic ring is preferred.

The aromatic amine (d) is broadly classified into (d-1) an aromatic amine in which a hydrogen atom on the aromatic ring is not replaced or is replaced with an electron donating group or a halogen group, and (d-2) an aromatic amine in which a hydrogen atom on the aromatic ring is replaced with an electron withdrawing group (excluding a halogen group).

((d-1) Aromatic Amine in which a Hydrogen Atom on the Aromatic Ring is not Replaced or is Replaced with an Electron Donating Group or a Halogen Group)

When a peroxyester compound (fa) and/or alkyl peroxide (fb), which are described later, are included as a component in the separately packed curable composition of the present invention, or when an additional compound (e.g., an organic peroxide) playing the role of an oxidizing agent of a chemical polymerization initiator or a photopolymerization initiator is not included as a component in the separately packed composition of the present invention, the aromatic amine (d-1) mainly plays the role of a reducing agent of the chemical polymerization initiator.

Examples of electron donating groups that can be contained in the aromatic amine (d-1) and replace a hydrogen atom on the aromatic ring include alkyl groups such as a methyl group, an ethyl group, an isopropyl group, and a tert-butyl group, an alkoxy group such as a methoxy group, an ethoxy group, and an isopropoxy group, an N,N-dialkylamino group in which an alkyl group such as a methyl group, an ethyl group, an isopropyl group and a tert-butyl group is substituted on the nitrogen atom, and the like. Examples of halogen groups that can be contained in the aromatic amine (d-1) and replace a hydrogen atom on the aromatic ring include a fluorine group, a chlorine group, and a bromine group.

Examples of the aromatic amine (d-1) include: aromatic primary amine compounds such as aniline and toluidine; aromatic secondary amine compounds such as aromatic substituted amino acid compounds represented by aromatic substituted glycines, such as N-methylaniline, N-methyl-p-toluidine, N-phenylglycine (NPG), N-tolylglycine (NTG), N,N-(3-methacryloyloxy-2-hydroxypropyl)phenylglycine (NPG-GMA), and alkali metal salts, alkaline earth metal salts, amine salts, and ammonium salts thereof; and aromatic tertiary amine compounds such as N,N-dimethylaniline (DMA), N,N-dibenzylaniline, N,N-dimethyl-p-toluidine (DMPT), N,N-diethyl-p-toluidine, N,N-di(2-hydroxy)ethyl)-p-toluidine (DEPT), N,N-dimethyl-p-ethylaniline, N,N-dimethyl-p-isopropylaniline, N,N-dimethyl-p-tert-butylaniline, N,N-dimethylanisidine, N,N-dimethylxylidine, N,N-dimethyl-3,5-di-t-butylaniline, N,N-dimethyl-p-chloroaniline, and N,N-dimethyl-p-fluoroaniline.

As the aromatic amine (d-1), in view of promoting polymerization, an aromatic secondary amine compound and an aromatic tertiary amine compound are preferred, and an aromatic tertiary amine compound is more preferred.

((d-2) Aromatic Amine Substituted with an Electron-Withdrawing Group (Excluding a Halogen Group))

When the photopolymerization initiator (g) (described later) is included in the separately packed curable composition of the present invention, the aromatic amine (d-2) mainly plays a role of promoting the polymerization of the polymerization initiator.

Examples of electron withdrawing groups that can be contained in the aromatic amine (d-2) and replace a hydrogen atom on the aromatic ring include a carboxylic acid ester group, such as a carboxy group, a methoxycarbonyl group, an ethoxycarbonyl group, a tert-butoxycarbonyl group, a methoxyethoxycarbonyl group, ethoxyethoxycarbonyl group, and a butoxyethoxycarbonyl group, an aldehyde group, an acetoxy group, a benzoyl group, and the like.

Examples of the aromatic amine (d-2) include N,N-dimethylaminobenzoic acid and alkyl esters thereof, such as methyl N,N-dimethylaminobenzoate, ethyl N,N-dimethylaminobenzoate (DMABAE), and butoxyethyl N,N-dimethylaminobenzoate (DMABABE), N,N-diethylaminobenzoic acid (DEABA) and alkyl esters thereof, N,N-dimethylaminobenzaldehyde (DMABAd), N,N-dimethylaminobenzophenone, and the like.

As the aromatic amine (d-2), DMABAE and DMABABE are preferable in view of polymerization promotion effect and handling.

The content of the aromatic amine compound (d) is preferably 0.01 to 5 parts by mass, more preferably 0.05 to 3 parts by mass, and further preferably 0.1 to 1 part by mass, based on 100 parts by mass of a total of the polymerizable monomers (a1) and (a2) having no acidic group and the polymerizable monomer (b) having an acidic group that are included in the first pack and the second pack (B). When the content of the aromatic amine (d) is within the above range, the curing time, the adhesion strength with the adherend, the pot life, and the color tone stability of the cured product tend to be excellent.

((e) At Least One Compound Selected from Sulfinic Acid and a Salt Thereof)

Because of including at least one compound (e) selected from sulfinic acid and a salt thereof in the separately packed curable composition of the present invention, the effect of promoting polymerization can be obtained. Further, since it is included in the second pack (B), the components included in the first pack (A) are not adversely affected during storage.

Examples of the at least one compound (e) selected from sulfinic acid and a salt thereof include: alkanesulfinic acids such as methanesulfinic acid, ethanesulfinic acid, propanesulfinic acid, hexanesulfinic acid, octanessulfinic acid, decanesulfinic acid, and dodecanesulfinic acid; cycloaliphatic sulfinic acids such as cyclohexanesulfinic acid and cyclooctanesulfinic acid; aromatic sulfinic acids such as benzenesulfinic acid, o-toluenesulfinic acid, p-toluenesulfinic acid, ethylbenzenesulfinic acid, decylbenzenesulfinic acid, dodecylbenzenesulfinic acid, 2,4,6-trimethylbenzenesulfinic acid, 2,4,6-triethylbenzenesulfinic acid, 2,4,6-triisopropylbenzenesulfinic acid, and naphthalenesulfinic acid; and alkali metal salts such as a sodium salt, a potassium salt, a lithium salt thereof, alkaline earth metal salts such as magnesium salt, a calcium salt, a barium salt thereof, and sulfinic acids such as amine salts, ammonium salts, pyridinium salts thereof. Among these, aromatic sulfinic acids and salts thereof are preferred, in view of the storage stability in the second pack (B) and the polymerization activity of the mixture obtained by mixing the first pack (A) and the second pack (B).

The content of the at least one compound (e) selected from sulfinic acid and a salt thereof is preferably 0.01 to 20 parts by weight, more preferably 0.1 to 10 parts by weight, and further preferably 1 to 5 parts by weight, based on 100 parts by mass of a total of the polymerizable monomers (a1) and (a2) having no acidic group and the polymerizable monomer (b) having an acidic group that are included in the first pack and the second pack (B). When the content of the compound (e) is within the above range, the curing time of the mixture, the polymerization properties in consideration of the pot life, and the adhesive strength of the obtained cured product tend to be excellent.

In the separately packed curable composition of the present invention, the total of the transition metal compound (c), the aromatic amine (d), and the least one compound (e) selected from sulfinic acid and a salt thereof is preferably 0.02 to 30 parts by mass, more preferably 0.1 to 20 parts by mass, and further preferably 1 to 10 parts by mass, based on 100 parts by mass of a total of the polymerizable monomers (a1) and (a2) having no acidic group and the polymerizable monomer (b) having an acidic group that are included in the first pack (A) and the second pack (B). When the total of the transition metal compound (c), the aromatic amine (d), and the compound (e) is in the above range, the curing time of the mixture, the polymerization properties in consideration of the pot life, the adhesive strength of the obtained cured product, the color tone stability tend to be excellent.

One preferred mode of the separately packed curable composition of the present invention includes: the first pack (A) containing (a1) the polymerizable monomer having no acidic group, (b) the polymerizable monomer having an acidic group, and (c) the transition metal compound; and the second pack (B) containing (a2) the polymerizable monomer having no acidic group, (d) the aromatic amine compound, and (e) the at least one compound selected from sulfinic acid and a salt thereof; and does not include another polymerization initiator. Even in such a case, a mixture obtained by mixing packs including the first pack (A) and the second pack (B) has a sufficient pot life, and it is possible to cure such a mixture. In this mode, the aromatic amine compound (d) is preferably the aromatic amine (d-1) in which a hydrogen atom on the aromatic ring is not replaced or is replaced with an electron donating group or a halogen group.

((fa) Peroxyester Compound and/or (fb) Alkyl Peroxide)

In a preferred mode, the second pack (B) included in the separately packed curable composition of the present invention includes a peroxyester compound (fa) and/or an alkyl peroxide (fb). By including the peroxyester compound (fa) and/or the alkyl peroxide (fb) in the separately packed curable composition of the present invention, the polymerization properties of the mixture prepared from the first pack (A) and the second pack (B) tend to improve, and the mechanical strength and adhesive strength of the obtained cured product tend to be excellent. Moreover, even when the peroxyester compound (fa) and/or an alkyl peroxide (fb) is/are stored in the second pack (B), the activity thereof tends not to deteriorate. When the second pack (B) includes the peroxyester compound (fa) and/or the alkyl peroxide (fb), the aromatic amine (d) is preferably the aromatic amine (d-1) in which a hydrogen atom on the aromatic ring is not replaced or is replaced with an electron donating group or a halogen group.

The peroxyester compound (fa) is not particularly limited, and any known peroxyester compound may be used as long as it has an acyl group on one of the peroxy groups (—OO— group) and a hydrocarbon group (or an organic group similar thereto) on the other peroxy group. Examples of the peroxyester compound (fa) include t-butyl peroxyneodecanoate, t-butyl peroxypivalate, t-butyl peroxyisobutyrate, t-butyl peroxymaleic acid, t-butyl peroxylaurate, t-butyl peroxyisopropyl monocarbonate, t-butyl peroxy-2-ethylhexyl monocarbonate, t-butyl peroxyisononanoate, t-butyl peroxyacetate, t-butyl peroxybenzoate, t-butylperoxy-2-ethylhexanoate, t-butylperoxy-3,5,5-trimethylhexanoate, t-butylperoxy-m-toluoylbenzoate, t-hexylperoxypivalate, 2,5-dimethyl-2,5-bis(2-ethylhexanoylperoxy)hexane, 1-cyclohexyl-1-methylethylperoxy-2-ethylhexanoate, t-hexylperoxy-2-ethylhexanoate, t-hexylperoxyisopropyl monocarbonate, t-hexylperoxybenzoate, cumylperoxyneodecanoate, 1,1,3,3-tetramethylbutylperoxyneodecanoate, 1-cyclohexyl-1-methylethylperoxyneodecanoate, t-hexylperoxyneodecanoate, 1,1,3,3-tetramethylbutylperoxy-2-ethylhexanoate, 2,5-dimethyl-2,5-bis(m-toluoylperoxy)hexane, 2,5-dimethyl-2,5-bis(benzoylperoxy)hexane, α,α-bis(neodecanoylperoxy)diisopropylbenzene, bis(t-butylperoxy)isophthalate, and the like.

The alkyl peroxide (fb) is not particularly limited, and any known alkyl peroxide may be used as long as it has a hydrocarbon group (or an organic group similar thereto) in both peroxy groups (—OO— groups). Examples of the alkyl peroxide (fb) include: for example, dialkyl peroxides such as di-t-butyl peroxide, di-t-hexyl peroxide, α,α'-bis(2-t-butylperoxyisopropyl)benzene, di-α-cumyl peroxide, 2,5-dimethyl-2,5-bis(t-butylperoxy)hexane, and t-butyl-α-cumyl peroxide; for example, alkyl peresters such as t-butyl peroxyneodecanoate, t-butyl peroxypivalate, t-butyl peroxy-2-ethylhexanoate, t-butyl peroxyisobutyrate, t-butyl peroxybenzoate, and t-butyl peroxyacetate; for example, 1,1-bis(t-butylperoxy)-2-methylcyclohexane, 1,1-bis(t-hexylperoxy)-3,3,5-trimethylcyclohexane, 1,1-bis(t-hexylperoxy)cyclohexane, 1,1-bis(t-butylperoxy)-3,3,5-trimethylcyclohexane, 1,1-bis(t-butylperoxy)cyclohexane, 2,2-bis(4,4-dibutylperoxycyclohexyl)propane, 2,2-bis(t-butylperoxy)butane, n-butyl-4,4-bis(t-butylperoxy)valerate, 1,1-di (t-butylperoxy)cyclohexane, and the like.

Among these peroxyester compounds (fa) and/or alkyl peroxides (fb), t-butyl peroxybenzoate, t-butyl peroxyisononanoate, and 1,1-di(t-butylperoxy) cyclohexane are preferred in view of storage stability and reactivity.

The compounds as the peroxyester compound (fa) and the alkyl peroxide (fb) may be used singly or in combination of two or more thereof. Further, a peroxyester compound (fa) and an alkyl peroxide (fb) may be used in combination.

In view of the curing time and pot life of the mixture prepared from the first pack (A) and the second pack (B), and the color tone stability of the cured product to be obtained, the content of the peroxyester compound (fa) and/or the alkyl peroxide (fb) is preferably 0.01 to 10 parts by mass, more preferably 0.05 to 3 parts by mass, and further preferably 0.1 to 1.5 parts by mass, based on 100 parts by mass of a total of the polymerizable monomers (a1) and (a2) having no acidic group and the polymerizable monomer (b) having an acidic group that are included in the first pack (A) and the second pack (B).

((g) Photopolymerization Initiator)

In a preferred mode, the second pack (B) included in the separately packed curable composition of the present invention includes a photopolymerization initiator (g). By including the photopolymerization initiator (g) in the curable composition, the polymerization properties of the mixture prepared from the first pack (A) and the second pack (B) are improved, and the mechanical strength and adhesive strength of the obtained cured product tend to be excellent. When the photopolymerization initiator (g) is included in the second pack (B), it is preferred that the aromatic amine (d) further include the aromatic amine (d-2) in which a hydrogen atom on the aromatic ring is replaced with an electron withdrawing group (excluding a halogen group).

As the photopolymerization initiator (g), any known photopolymerization initiator can be used without limitation. For example, an α-diketone/reducing agent, a ketal/reducing agent, a thioxanthone/reducing agent, an acylphosphine oxide compound, and the like can be used.

Examples of the α-diketone include diacetyl, 2,3-pentadione, 2,3-hexadione, benzyl, 4,4'-dimethoxybenzyl, 4,4'-diethoxybenzyl, 4,4'-oxybenzyl, 4,4'-dichlorobenzyl, 4-nitrobenzyl, α-naphthyl, β-naphthyl, camphorquinone (CQ), camphorquinonesulfonic acid, camphorquinonecarboxylic acid, 1,2-cyclohexanedione, methylglyoxal, phenylglyoxal, pyruvic acid, benzoylformic acid, phenylpyruvic acid, methyl pyruvate, ethyl benzoylformate, methyl phenylpyruvate, butyl phenylpyruvate, and the like.

Examples of the ketal include benzyl dimethyl ketal, benzyl diethyl ketal, and the like.

Examples of the thioxanthone include 2-chlorothioxanthone, 2,4-diethylthioxanthone, 2-hydroxy-3-(9-oxy-9H-thioxanthen-4-yloxy)-N,N,N-trimethyl-propanaminium chloride, 2-hydroxy-3-(1-methyl-9-oxy-9H-thioxanthen-4-yloxy)-N,N,N-trimethyl-propanaminium chloride, 2-hydroxy-3-(9-oxo-9H-thioxanthen-2-yloxy)-N,N,N-trimethyl-propanaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, 2-hydroxy-3-(1,3,4-trimethyl-9-oxo-9H-thioxanthen-2-yloxy)-N,N,N-trimethyl-1-propaneaminium chloride, and the like.

Examples of the acylphosphine oxide compound include benzoyldimethoxyphosphine oxide, benzoylethoxyphenylphosphine oxide, benzoyldiphenylphosphine oxide, 2-methylbenzoyldiphenylphosphine oxide, 2,4,6-trimethylbenzoyldiphenylphosphine oxide, bis(2,6-dimethoxybenzoyl)-2,4,4-trimethylpentylphosphine oxide, bis(2,4,6-trimethylbenzoyl)-phenylphosphine oxide, and the like.

Examples of the reducing agent include:

hydrogen peroxide and Michler ketone;

aldehydes such as citronellal, lauryl aldehyde, phthaldialdehyde, dimethylaminobenzaldehyde, and terephthalaldehyde;

mercaptans such as 2-mercaptobenzoxazole, decanethiol, 3-mercaptopropyltrimethoxysilane, 4-mercaptoacetophenone, thiosalicylic acid, thiobenzoic acid; and an aromatic amine compound (d) such as the aromatic amine compound (d-2) described above.

Among the above-described examples of the photopolymerization initiator (g), a photopolymerization initiator containing a camphorquinone and/or an acylphosphine oxide compound is preferred, and in particular, a photopolymerization initiator containing camphorquinone having an absorption wavelength at 468 nm is more preferred in view of having an absorption wavelength in the visible light region and being polymerizable by visible light.

Examples of the photopolymerization initiator containing camphorquinone/reducing agent include a polymerization initiator containing camphorquinone/aromatic amine compound (d), a photopolymerization initiator containing camphorquinone/peroxide, a photopolymerization initiator containing camphorquinone/aldehyde, and a polymerization initiator containing camphorquinone/mercaptan. Of these, a polymerization initiator containing camphorquinone/aromatic amine (d) is preferred, and a polymerization initiator containing camphorquinone/aromatic amine (d-2) is more preferred.

These initiators as the photopolymerization initiator (g) may be used singly or in combination of two or more thereof.

In addition, when the photopolymerization initiator (g) is included in the separately packed curable composition of the present invention, the photopolymerization initiator (g) is included in another pack other than the first pack (A) and the second pack (B) (e.g., a third pack) in a preferred mode. For example, when camphorquinone and an acylphosphine oxide compound are included as the photopolymerization initiator (g), polymerization of the polymerizable monomer (a2) having no acidic group contained in the second pack (B) during storage tends to be able to be suppressed more.

The content of the photopolymerization initiator (g) is preferably 0.001 to 5 parts by mass, more preferably 0.005 to 2 parts by mass, and further preferably 0.01 to 1 part by mass, based on 100 parts by mass of a total of the polymerizable monomers (a1) and (a2) having no acidic group and the polymerizable monomer (b) having an acidic group. If the content of the photopolymerization initiator (g) is less than this lower limit, curing of the mixture prepared from the first pack (A) and the second pack (B) may not proceed sufficiently. If the content is more than this upper limit, the mixture may develop a color tone derived from the photopolymerization initiator, and further, the polymerizable monomer in the second pack (B) may be more easily polymerized during storage.

((h) Filler)

The filler (h) may be included in at least one of the first pack (A) and the second pack (B) of the separately packed curable composition of the present invention. By including the filler (h) in the curable composition, it is possible, for example, to adjust the fluidity and consistency, the color tone, curability, and the like of the mixture prepared from the first pack (A) and the second pack (B), to impart radiodensity, and to improve the mechanical strength of the obtained cured product. As the filler (h), a general filler used in the dental field can be used. The filler (h) is generally broadly classified into an organic filler and an inorganic filler.

The organic filler may be a powdered polymer filler obtained by pulverization of a polymer or by dispersion polymerization, and a filler obtained by polymerizing a polymerizable monomer with a crosslinking agent and then pulverizing the resulting polymer. Examples of the organic filler include a fine powder of a homopolymer or copolymer of a polymerizable monomer, such as polymethyl methacrylate (PMMA), polyethyl methacrylate, polypropyl methacrylate, polybutyl methacrylate (PBMA), polyvinyl acetate (PVAc), polyethylene glycol (PEG), polypropylene glycol (PPG), polyvinyl alcohol (PVA), polyurethane, polyurea, methyl methacrylate-ethyl methacrylate copolymer, crosslinked polymethyl methacrylate, crosslinked polyethyl methacrylate, ethylene-vinyl acetate copolymer, and styrene-butadiene copolymer. Further, the organic filler may also be a product obtained by adding a component such as a known pigment, a biologically active component, a polymerization initiator, and the like during the preparation of the organic filler.

Examples of the inorganic filler include a fine powder of various glasses (mainly composed of silicon dioxide, containing oxides such as heavy metals, boron and aluminum as necessary), various ceramics, diatomaceous earth, kaolin, clay mineral (montmorillonite, etc.), activated clay, synthetic zeolite, mica, calcium fluoride, ytterbium fluoride, calcium carbonate, calcium phosphate, aluminum sulfate, barium sulfate, calcium sulfate, zirconium dioxide, titanium dioxide, aluminum oxide, boron oxide, barium oxide, lanthanum oxide, strontium oxide, zinc oxide, calcium oxide, lithium oxide, sodium oxide, bismuth oxide, yttrium oxide, calcium phosphate, hydroxyapatite, aluminum hydroxide, sodium fluoride, potassium fluoride, sodium monofluorophosphate, lithium fluoride, ytterbium fluoride, and the like. Specific examples of such inorganic fillers include, for example, a fine powder of barium borosilicate glass (such as Kimble RAY-SORB T3000, Schott 8235, Schott GM27884 and Schott GM39923), a fine powder of strontium boroaluminosilicate glass (such as RAY-SORB T4000, Schott G018-093 and Schott GM32087), a fine powder of lanthanum glass (such as Schott GM31684), a fine powder of fluoroaluminosilicate glass (such as Schott G018-091 and Schott G018-117), and a fine powder of boroaluminosilicate glasses containing zirconium and/or cesium (such as Schott G018-307, G018-308 and G018-310).

It is also possible to use an organic/inorganic composite filler obtained by: adding a polymerizable monomer to the above-mentioned inorganic fillers in advance to form a paste, then polymerizing and curing, and grinding the resultant product. As a specific example of an organic-inorganic composite filler, there may be mentioned a filler (TMPT.f) obtained by, from among the inorganic fillers, polymerizing and coating fine powder silica or zirconium oxide with a polymerizable monomer having trimethylolpropane tri(meth)acrylate (TMPT) as a main component, and then pulverizing the obtained polymer.

Further, one preferred mode of the dental composite resin is a dental composition incorporating a microfiller having a particle size of 0.1 μm or less. Preferred materials for fillers having such a small particle size include silica (e.g., AEROSIL (trade name)), alumina, zirconia and titania. Incorporating an inorganic filler having such a small particle size is advantageous in imparting a polishing smoothness and abrasion resistance to the cured product.

These fillers are subjected to surface treatment with a silane coupling agent or the like according to the purpose. When using an inorganic filler or an organic-inorganic composite filler, it is preferred to treat the filler surface with a known surface treating agent to improve the affinity and dispersibility with the polymerizable monomer used in the present invention. As such a surface treatment agent, a known silane coupling agent can be used without limitation. For example, γ-methacryloxyalkyltrimethoxysilane (number of carbons between methacryloxy group and silicon atom: 3 to 12), γ-methacryloxyalkyltriethoxysilane (number of carbons between methacryloxy group and silicon atom): 3 to 12), or an organosilicon compound such as vinyltrimethoxysilane, vinylethoxysilane, and vinyltriacetoxysilane is used. The concentration of the surface treatment agent is usually 0.1 to 20 parts by mass, and preferably 0.5 to 10 parts by mass, based on 100 parts by mass of the filler. In addition to the silane coupling agent, a surface treatment may be performed with a titanate coupling agent, an aluminate coupling agent, a zirco-aluminate coupling agent, or the like. Furthermore, the radical polymerizable monomer may be graft-polymerized onto the surface of the filler particles. As the surface treatment method, a known method can be used without particular limitation.

Such a filler (h) can be appropriately added according to the use of the dental material. The fillers as the filler (h) may be used singly or in combination of two or more thereof. Moreover, the filler (h) may be included in one or both of the first pack (A) and the second pack (B). When the filler (h) is included in both the first pack (A) and the second pack (B), the filler included in the first pack (A) and the filler included in the second pack (B) may be the same or different.

The content of the filler (h) can be appropriately set according to its use. For example, when the separately packed curable composition of the present invention is to be used as a dental cement, a self-adhesive composite resin, or the like, the content of the filler (h) is preferably 10 to 900 parts by mass, more preferably 40 to 400 parts by mass, and further preferably 60 to 240 parts by mass, based on 100 parts by mass of a total of the polymerizable monomers (a1) and (a2) having no acidic group and the polymerizable monomer (b) having an acidic group that are included in the first pack (A) and the second pack (B).

(Other Components)

The first pack (A) and/or the second pack (B) of the separately packed curable composition of the present invention may include components other than those described above as appropriate and in accordance with the intended purpose as long as such components do not impair the storage stability of the first pack (A) and the second pack (B) and do not impair the curing function of a curable composition.

For example, the first pack (A) and/or the second pack (B) may include various stabilizers, such as a polymerization inhibitor and an ultraviolet absorber, in order to improve storage stability and the like, and in order to adjust the color tone may include known pigments, dyes, fluorescent agents, and the like. In addition, the first pack (A) and/or the second pack (B) may include a calcium-containing compound such as calcium chloride, a fluorine-containing compound such as sodium fluoride, an antifungal agent, an antibacterial agent, a therapeutic and biologically active ingredient. Furthermore, in order to improve the strength of the obtained cured product, the first pack (A) and/or the second pack (B) may include a known reinforcing material such as fiber. Further, the first pack (A) and/or the second pack (B) may also include a solvent such as acetone, ethanol, water, and the like.

The amount of each of the other components blended is preferably 0.00001 to 10 parts by mass, more preferably 0.00005 to 5 parts by mass, and further preferably 0.0001 to 1 part by mass, based on 100 parts by mass of a total of the polymerizable monomers (a1) and (a2) having no acidic group and the polymerizable monomer (b) having an acidic group that are included in the first pack (A) and the second pack (B), in view of not impairing the effects of the present invention and exhibiting the characteristics of those other components.

The separately packed curable composition of the present invention is divided and separately packaged in a plurality of packs including the first pack (A) and the second pack (B)

described above. Examples of the form of those packs include liquids, pastes, and the like. In view of ease of handling, the separately packed curable composition of the present invention is preferably a paste for both the first pack (A) and the second pack (B). When the separately packed curable composition of the present invention is a two-pack paste composition in which both the first pack (A) and the second pack (B) are pastes, it is suitable for a dental adhesive resin cement. Moreover, the separately packed curable composition of the present invention may include other packs such as a third pack. The mixing mass ratio between the first pack (A) and the second pack (B) can be appropriately set based on the curability of the mixture to be obtained and the time available for the bonding operation (work life), but it is preferably 1:10 to 10:1, more preferably 1:5 to 5:1, and further preferably 1:2 to 2:1.

A mixture obtained by mixing each of the separate packs of the separately packed curable composition of the present invention can cure at ordinary temperature or body temperature (40° C.), and the resulting cured product can be used for dental treatment.

In addition, in the case of including a photopolymerization initiator as a component of the separately packed curable composition, a desired cured product can be obtained by processing the mixture obtained by mixing the packs into a predetermined shape, then irradiating it with visible light for a predetermined time using a known light irradiation device. The conditions such as the irradiation time and the irradiation intensity can be appropriately changed in accordance with the curability of the separately packed curable composition of the present invention. Moreover, the mechanical properties of the obtained cured product can also be improved by heat-treating the cured product after light irradiation under more appropriate conditions.

The separately packed curable composition of the present invention has a sufficient pot life and an appropriate curing time, its curing time hardly changes even after long-term storage at room temperature or higher, and it has excellent storage stability. As a result, the separately packed curable composition of the present invention can be suitably used for various dental treatment applications, such as, for example, a dental adhesive resin cement, a dental composite resin (including a self-adhesive composite resin), a dental bonding material, a dental backing material, a dental root filler, an orthodontic adhesive, a mobile tooth fixing material, a tooth fissure sealant (dental sealant), a temporary dental cement, and the like.

The separately packed curable composition of the present invention can be used, for example, by a method generally known as a method of using a dental material. For example, when the separately packed curable composition of the present invention is used as a dental adhesive resin cement, a self-adhesive composite resin, or the like, a mixture obtained by mixing the packs included in the separately packed curable composition can be applied alone to an adhesion surface. Further, when the separately packed curable composition of the present invention is used as the dental material, it may be used together with another dental material. For example, a mixture prepared from the separately packed curable composition of the present invention can be applied after the surface of the adherend has been treated with another composition, such as a bonding material or a primer.

In view of a sufficient pot life, appropriate polymerization properties, and excellent storage stability, it is preferred that a delay in the curing time of the separately packed curable composition of the present invention after storage at 55° C. for 3 weeks is no greater than 1 minute compared with the curing time immediately after preparation. The curing time at 37° C. of the separately packed curable composition of the present invention is preferably 0.5 to 5 minutes, more preferably 1 to 4 minutes, and further preferably 1.5 to 3 minutes. Furthermore, the pot life at 23° C. of the separately packed curable composition of the present invention is preferably 120 to 600 seconds, more preferably 150 to 480 seconds, and further preferably 180 to 420 seconds. The pot life, the curing time, and the storage stability of the separately packed curable composition of the present invention are evaluated by the methods described in Examples.

The present invention also includes a polymerization initiator kit comprising: a first member including (c) the transition metal compound; and a second member including (d) an aromatic amine compound and (e) at least one compound selected from sulfinic acid and a salt thereof, the aromatic amine compound (d) and the at least one compound (e) being accommodated together or separately.

The present invention also includes a curable composition kit comprising: (c) a first member including a transition metal compound; and a second member including (d) an aromatic amine compound and (e) at least one compound selected from sulfinic acid and a salt thereof, the aromatic amine compound (d) and the at least one compound (e) being accommodated together or separately, wherein at least one polymerizable monomer is included in either the first member or the second member, or included in another member other than the first member and the second member.

In the second member of the polymerization initiator kit and the curable composition kit of the present invention, the aromatic amine compound (d) and the least one compound (e) selected from sulfinic acid and a salt thereof may be accommodated together in the same member, or may be separately accommodated and constitute the second member.

Further, in the polymerization initiator kit and the curable composition kit of the present invention, the transition metal compound (c), the aromatic amine compound (d), and the least one compound (e) selected from sulfinic acid and a salt thereof can be the same as that used in the separately packed curable composition of the present invention described above.

Examples of the polymerizable monomer included in the curable composition kit of the present invention include the polymerizable monomer (a1) having no acidic group, the polymerizable monomer (b) having no acidic group, and the polymerizable monomer (a2) having no acidic group used in the separately packed curable composition of the present invention described above. For these, it is preferred that the first member include the polymerizable monomer (a1) having no acidic group and the polymerizable monomer (b) having no acidic group, and that the second member include the polymerizable monomer (a2) having no acidic group. Further, the polymerizable monomer may be included in another member other than the first member and the second member. In that case, the polymerizable monomers may be dividedly and separately accommodated in members for constituting another member so as to form a corresponding structure to the above-mentioned first pack and second pack.

In the polymerization initiator kit and the curable composition kit of the present invention, the other components included in the separately packed curable composition of the present invention described above may be included. For example, the peroxyester compound (fa) and/or the alkyl peroxide (fb) may be separately accommodated in the first member or the second member or another member so as to form a corresponding structure to the above-mentioned first pack and second pack.

In the polymerization initiator kit and the curable composition kit of the present invention, the form in which each component is separated is not particularly limited. For example, each member may be provided in an integral container in which the members are separated by a partition so that the components do not contact each other. Alternatively, each component may be contained in a separate container.

For the polymerization initiator kit and the curable composition kit of the present invention, examples of the accommodating member include a sealable gas-barrier resin container or glass syringe in order to prevent volatilization and scattering of the various components. The amount to be accommodated in the container may be an amount sufficient for only one-time use, or may be an amount that is for multiple use.

EXAMPLES

Hereinafter, the present invention will be described in detail with reference to examples and comparative examples, but the present invention is not limited to these examples.

The abbreviations of the compounds used in the examples are shown below.

[(a) Polymerizable Monomer Having No Acidic Group]

UDMA: 1,6-Bis(methacryloxyethyloxycarbonylamino)-2,2,4-trimethylhexane (self-prepared compound of HEMA and 2,2,4-trimethylhexyl diisocyanate in a 2:1 ratio in accordance with a known urethanization method)

TEGDMA: Triethylene glycol dimethacrylate (manufactured by Shin Nakamura Chemical Co., Ltd.) HEMA: Hydroxyethyl methacrylate (manufactured by Mitsubishi Chemical Corporation)

[(b) Polymerizable Monomer Having an Acidic Group]

4-MET: 4-Methacryloyloxyethyl trimellitic acid (manufactured by Sun Medical Co., Ltd.)

MDP: 10-Methacryloyloxydecyl dihydrogen phosphate (manufactured by FUJIFILM Wako Pure Chemical Corporation)

[(c) Transition Metal Compound]

VO(acac)$_2$: Vanadyl(IV) acetylacetonate (manufactured by Tokyo Chemical Industry Co., Ltd., used after pulverization by a mortar before use)

V(acac)$_3$: Vanadium(III) acetylacetonate (manufactured by Sigma-Aldrich)

[(d) Aromatic Amine Compound]

DMPT: N,N-dimethyl-p-toluidine (manufactured by FUJIFILM Wako Pure Chemical Corporation)

DEPT: N,N-diethanol-p-toluidine (manufactured by FUJIFILM Wako Pure Chemical Corporation)

MA: N-methylaniline (manufactured by FUJIFILM Wako Pure Chemical Corporation)

NPGS: N-phenylglycine sodium salt (manufactured by Tokyo Chemical Industry Co., Ltd.)

[(e) at Least One Compound Selected from Sulfinic Acid and a Salt Thereof]

p-TSS: Sodium p-toluenesulfinate (manufactured by FUJIFILM Wako Pure Chemical Corporation, dried at 70° C. under reduced pressure after purchase, and pulverized by a mortar)

[(fa) Peroxyester Compound and/or (Fb)Alkyl Peroxide]

tBPB: t-Butyl peroxybenzoate (trade name "Luperox® P", manufactured by Sigma-Aldrich)

tBPiN: t-Butyl peroxyisononanoate (trade name "Luperox 270", manufactured by ARKEMA Yoshitomi Ltd.)

DtBPOC: 1,1-Di(t-butylperoxy)cyclohexane (trade name "Luperox 331XL", manufactured by ARKEMA Yoshitomi Ltd.)

[Diacyl Peroxide]

BPO: Benzoyl peroxide (manufactured by Tokyo Chemical Industry Co., Ltd.)

[(g) Photopolymerization Initiator]

CQ: d,l-Camphorquinone (manufactured by FUJIFILM Wako Pure Chemical Corporation)

DMABAE: Ethyl N,N-dimethylbenzoate ((manufactured by FUJIFILM Wako Pure Chemical Corporation)

[(h) Filler]

F1: Silane-treated barium glass powder, silane-treated fluoroaluminosilicate powder, etc. (trade names "8235", "G018-117", etc., manufactured by SCHOTT)

R812: Fine particle silica (trade name "AEROSIL R812", manufactured by Nippon Aerosil Co., Ltd.)

[Other Components: Polymerization Inhibitor]

BHT: 2,6-Di-t-butyl-4-methylphenol (manufactured by Tokyo Chemical Industry Co., Ltd.)

MEHQ: 4-Methoxyphenol (FUJIFILM Wako Pure Chemical Corporation)

<Measurement Method of Curing Time and Pot Life>

The curing time and the pot life in each examples and comparative examples were measured by differential thermal analysis using a differential scanning calorimeter (DSC). As the measuring apparatus, a DSC 3500 Sirius (manufactured by NETZSCH) was used.

Specifically, the first pack (A) and the second pack (B) in equal amounts were mixed on dental kneading paper with a dental spatula for 10 seconds at room temperature set to 20 to 25° C. to obtain a polymerizable mixture. The obtained polymerizable mixture was filled in an sample pan made of Al for DSC measurement.

When measuring the pot life, the sample pan filled with the polymerizable mixture was placed in a DSC thermostat set to 23±1° C., and measurement was started 40 seconds after the start of kneading. The time until the point at which the temperature started to rise due to the start of curing was recorded. The sum of the time recorded by DSC and the 40 seconds before the start of measurement was calculated as the pot life.

When measuring the curing time, the Al sample pan filled with the polymerizable mixture was placed in a DSC thermostat set at 37±1° C. just before measurement, and measurement was started 40 seconds after the start of kneading. The time until the point at which the temperature started to rise due to the start of the curing reaction of the polymerizable mixture and reached the maximum temperature was recorded as the pot life.

<Storage Stability Test>

The first pack (A) and the second pack (B) immediately after preparation which were separate from those for measuring the pot life and the curing time by the above methods were placed in a separately-prepared thermostat at 55° C. after measuring the pot life and the curing time. They are taken out after storing for one week, two weeks, and three weeks, and the curing time was measured in accordance with the method described above. During the storage period, the first pack (A) was stirred once every two to three days with a dental spatula to keep the system uniform.

If the pot life is 120 seconds or more, it can be determined that the tested polymerizable mixture has a sufficient pot life. Moreover, if the curing time is within 3 minutes, it can be determined that the tested polymerizable mixture has appropriate curability. Furthermore, if the curing time delay of the tested polymerizable mixture after the storage stability test is within 1 minute compared to that before the test, it can be determined that the deterioration in the polymerization properties is low and the storage stability is excellent.

Examples 1 and 2, Comparative Examples 1 to 3

The first pack and the second pack were prepared by mixing the components in accordance with the formulations shown in the following Table 1 (the numerical values in the table are in parts by mass), and a separately packed curable composition was thus produced that had a total mass ratio between the first pack and the second pack of 1:1.

On each of the obtained separately packed curable compositions, the curing time and the pot life were measured and the storage stability was evaluated in accordance with the methods described above. The results are shown in Table 1.

Examples 3 to 14

The first pack and the second pack were prepared by mixing the components in accordance with the formulations shown in the following Table 2 (the numerical values in the table are in parts by mass), and a separately packed curable composition was thus produced that had a total mass ratio between the first pack and the second pack of 1:1.

On each of the obtained separately packed curable compositions, the curing time and the pot life were measured and the storage stability was evaluated in accordance with the methods described above. The results are shown in Table 2.

TABLE 1

|  |  |  |  | Example 1 | Example 2 | Comparative Example 1 | Comparative Example 2 | Comparative Example 3 |
|---|---|---|---|---|---|---|---|---|
| First pack | (a) Polymerizable monomer having no acidic group | UDMA | 60 | 60 | 60 | 60 | 60 |
| | | TEGDMA | 20 | 20 | 20 | 20 | 20 |
| | (b) Polymerizable monomer having an acidic group | 4-MET | 20 | 20 | 20 | 20 | 20 |
| | (c) Vanadium compound | VO(acac)2 | 0.1 | 0.1 | | 0.1 | |
| | Diacyl peroxide | BPO | | | 3 | | |
| | Polymerization inhibitor | BHT | 0.2 | 0.2 | 0.2 | 0.2 | 0.2 |
| | | MEHQ | 0.1 | 0.1 | 0.1 | 0.1 | 0.1 |
| | (h) Filler | R812 | 5 | 5 | 5 | 5 | 5 |
| | | F1 | 180 | 180 | 180 | 180 | 180 |
| Second pack | (a) Polymerizable monomer having no acidic group | UDMA | 70 | 70 | 70 | 70 | 70 |
| | | TEGDMA | 30 | 30 | 30 | 30 | 30 |
| | (d) Aromatic amine compound | DEPT | 0.3 | 0.3 | 0.2 | | 0.3 |
| | Peroxyester | tBPB | 1 | | | 1 | 1 |
| | Diacyl peroxide | BPO | | 3 | | | |
| | Polymerization inhibitor | BHT | 0.2 | 0.2 | 0.2 | 0.2 | 0.2 |
| | | MEHQ | 0.1 | 0.1 | 0.1 | 0.1 | 0.1 |
| | (e) Sulfinic acid compound | pTSS | 5 | 5 | 5 | 5 | 5 |
| | (h) Filler | R812 | 15 | 15 | 15 | 15 | 15 |
| | | F1 | 165 | 165 | 165 | 165 | 165 |
| Pot life (23° C.) (sec) | | | 282 | 486 | 192 | >600 | >600 |
| Curing time (37° C.) (min) | | | 2.0 | 4.7 | 1.5 | 8.8 | >10 |
| After storing at 55° C. for 1 week | | | 2.1 | — | 1.9 | — | — |
| After storing at 55° C. for 2 weeks | | | 1.5 | — | 3.0 | — | — |
| After storing at 55° C. for 3 weeks | | | 1.5 | — | 3.3 | — | — |

As shown in Table 1, the separately packed curable composition of the present invention produced in Example 1 has a sufficient pot life and an appropriate curing time. In addition, there was no delay in curing time, and excellent storage stability was exhibited. On the other hand, the separately packed curable composition produced in Comparative Example 1 had a sufficient pot life and curability, but the curing time after the storage stability test was delayed to double or more. Furthermore, the separately packed curable composition produced in Comparative Example 2 did not have an appropriate curing time, and Comparative Example 3 did not cure within 10 minutes. In addition, from Example 2, it can be seen that the curable composition including BPO in the second pack did not significantly reduce the curing time after storage, but that a sufficient curing time was not obtained. From this, it is understood that BPO is not preferred as a peroxide to be included in the second pack.

water, the amount of water being 10 g per piece of the cure product, and stored at 37° C. for 1 week. The degree of change (color difference) in color tone between before and after the storing was determined. As a result, the cured product of Example 1 was confirmed to have a smaller degree of discoloration.

TABLE 2

|  |  |  | Example 3 | Example 4 | Example 5 | Example 6 | Example 7 | Example 8 | Example 9 | Example 10 | Example 11 | Example 12 | Example 13 | Example 14 |
|---|---|---|---|---|---|---|---|---|---|---|---|---|---|---|
| First pack | (a) Polymerizable monomer having no acidic group | UDMA | 60 | 60 | 60 | 60 | 60 | 60 | 60 | 60 | 60 | 40 | 60 | 60 |
|  |  | HEMA | 20 | 20 | 20 | 20 | 20 | 20 | 20 | 20 | 20 | 40 | 20 | 20 |
|  | (b) Polymerizable monomer having an acidic group | 4-MET | 20 | 20 | 20 | 20 | 20 | 20 | 20 | 20 | 20 |  | 20 | 20 |
|  |  | MDP |  |  |  |  |  |  |  |  |  | 20 |  |  |
|  | (c) Vanadium compound | VO(acac)2 | 0.1 |  | 0.1 | 0.1 | 0.1 | 0.1 | 0.1 | 0.1 | 0.1 | 0.6 | 0.1 | 0.1 |
|  |  | V(acac)3 |  | 0.1 |  |  |  |  |  |  |  |  |  |  |
|  | Polymerization inhibitor | BHT | 0.2 | 0.2 | 0.2 | 0.2 | 0.2 | 0.2 | 0.2 | 0.2 | 0.2 | 0.2 | 0.2 | 0.2 |
|  |  | MEHQ | 0.1 | 0.1 | 0.1 | 0.1 | 0.1 | 0.1 | 0.1 | 0.1 | 0.1 | 0.1 | 0.1 | 0.1 |
|  | (h) Filler | R812 | 5 | 5 | 5 | 5 | 5 | 5 | 5 | 5 | 5 | 5 | 5 | 5 |
|  |  | F1 | 180 | 180 | 180 | 180 | 180 | 180 | 180 | 180 | 180 | 180 | 180 | 180 |
| Second pack | (a) Polymerizable monomer having no acidic group | UDMA | 70 | 70 | 70 | 70 | 70 | 70 | 70 | 70 | 70 | 70 | 70 | 70 |
|  |  | TEGDMA | 30 | 30 | 30 | 30 | 30 | 30 | 30 | 30 | 30 | 30 | 30 | 30 |
|  | (d) Aromatic amine compound | DEPT | 0.3 | 0.3 |  |  |  | 0.3 | 0.3 | 0.3 | 0.3 | 0.3 | 0.3 | 0.3 |
|  |  | DMPT |  |  | 0.3 |  |  |  |  |  |  |  |  |  |
|  |  | MA |  |  |  | 0.2 |  |  |  |  |  |  |  |  |
|  |  | NPGS |  |  |  |  | 1.5 |  |  |  |  |  |  |  |
|  | (fa) Peroxyester compound | tBPB | 1 | 1 | 1 | 1 | 1 | 1 |  |  |  | 1 | 1 |  |
|  |  | tBPiN |  |  |  |  |  |  |  | 1 |  |  |  |  |
|  | (fb) Alkyl peroxide | DtBPOC |  |  |  |  |  |  |  |  | 1 |  |  |  |
|  | (g) Photopolymerization initiator | CQ |  |  |  |  |  |  |  |  |  |  | 0.1 | 0.1 |
|  |  | DMABAE |  |  |  |  |  |  |  |  |  |  | 0.6 | 0.6 |
|  | Polymerization inhibitor | BHT | 0.2 | 0.2 | 0.2 | 0.2 | 0.2 | 0.2 | 0.2 | 0.2 | 0.2 | 0.2 | 0.2 | 0.2 |
|  |  | MEHQ | 0.1 | 0.1 | 0.1 | 0.1 | 0.1 | 0.1 | 0.1 | 0.1 | 0.1 | 0.1 | 0.1 | 0.1 |
|  | (e) Sulfinic acid compound | pTSS | 5 | 5 | 5 | 5 | 5 | 9 | 5 | 5 | 5 | 5 | 5 | 5 |
|  | (h) Filler | R812 | 15 | 15 | 15 | 15 | 15 | 15 | 15 | 15 | 15 | 15 | 15 | 15 |
|  |  | F1 | 165 | 165 | 165 | 165 | 163.5 | 161 | 165 | 165 | 165 | 165 | 165 | 165 |
| Pot life (23° C.) (sec) |  |  | 324 | 304 | 306 | 268 | 250 | 228 | 348 | 424 | 412 | 190 | 210 | 276 |
| Curing time (37° C.) (min) |  |  | 2.6 | 1.8 | 1.8 | 1.2 | 1.9 | 1.7 | 2.8 | 2.3 | 1.8 | 1.5 | 1.5 | 2.3 |
| After storing at 55° C. for 1 week |  |  | 1.9 | 1.2 | 1.8 | 1.1 | 1.1 | 1.2 | 1.9 | 1.2 | 1.3 | 2.0 | 1.5 | 1.9 |
| After storing at 55° C. for 2 weeks |  |  | 1.5 | 1.3 | 1.4 | 0.8 | 0.8 | 1.1 | 2.3 | 1.1 | 1.1 | 1.4 | 1.9 | 1.7 |
| After storing at 55° C. for 3 weeks |  |  | 2.1 | 1.5 | 1.4 | 0.9 | 1.4 | 1.3 | 1.9 | 1.7 | 1.3 | 2.0 | 2.1 | 2.2 |

As shown in Table 2, the separately packed curable compositions of the present invention produced in Examples 3 to 14 have a sufficient pot life and an appropriate curing time. In addition, there was no delay in curing time, and excellent storage stability was exhibited.

Example 15

The separately packed curable composition of Example 15 was prepared that had the same composition as the separately packed curable composition of Example 1 except that vanadyl(IV) acetylacetonate was changed to the same amount of copper acetate (Cu(OAc)$_2$).

<Color Tone Check Test>

For the separately packed curable compositions of Example 1 and Example 15, the first pack and the second pack were mixed and a cured product having a diameter of 15 mm and a thickness of 1 mm was produced therefrom. The color of the cured product was visually observed.

As a result, the cured product of the separately packed curable composition of Example 1 including vanadyl(IV) acetylacetonate was milky white, whereas the cured product of the separately packed curable composition including Cu(OAc)$_2$ was light blue.

<Discoloration Test>

Next, a discoloration test was performed using each of the cured products of Example 1 and Example 15. In the discoloration test, the cure product was immersed in distilled As clear from the above, the curable composition of the present invention including a vanadium compound as a transition metal compound exhibits a milky white color closer to the color of teeth compared to a composition including a copper compound, and suppresses the discoloration of the cured product. The former can therefore be said to be suitable for dental use.

The invention claimed is:

1. A polymerization initiator kit comprising:
    a first member including:
        (b) a polymerizable monomer having an acidic group, and
        (c) a transition metal compound; and
    a second member including:
        (d) an aromatic amine compound,
        (e) at least one compound selected from sulfinic acid and a salt thereof, and
        (fa) a peroxyester compound and/or (fb) an alkyl peroxide,
        the aromatic amine compound (d) and the at least one compound (e) being accommodated together or separately.

2. The polymerization initiator kit according to claim 1, which is a curable composition kit
    wherein at least one polymerizable monomer is included in either one of the first member or the second member, or included in another member other than the first member and the second member.

3. The polymerization initiator kit according to claim 1, which is a separately packed curable composition, wherein:
- a first pack (A) comprises the first member and further contains:
  - (a1) a polymerizable monomer having no acidic group; and
- a second pack (B) comprises the second member and further contains:
  - (a2) a polymerizable monomer having no acidic group.

4. The polymerization initiator kit according to claim 3, wherein the metal constituting the transition metal compound (c) is an early transition metal.

5. The polymerization initiator kit according to claim 3, wherein the transition metal compound (c) is a vanadium compound.

6. The polymerization initiator kit according to claim 3, wherein the second pack (B) contains a photopolymerization initiator (g).

7. The polymerization initiator kit according to claim 3, wherein at least one of the first pack (A) and the second pack (B) contains a filler (h).

8. The polymerization initiator kit according to claim 3, wherein a total of the transition metal compound (c), the aromatic amine (d), and the at least one compound (e) selected from sulfinic acid and a salt thereof is 0.02 to 30 parts by mass based on 100 parts by mass of a total of the polymerizable monomers (a1) and (a2) having no acidic group and the polymerizable monomer (b) having an acidic group that are included in the first pack (A) and the second pack (B).

9. The polymerization initiator kit according to claim 3, wherein a content of the transition metal compound (c) in the first pack (A) is 0.001 to 5 parts by mass based on 100 parts by mass of a total of the polymerizable monomers (a1) and (a2) having no acidic group and the polymerizable monomer (b) having an acidic group that are included in the first pack (A) and the second pack (B).

10. The polymerization initiator kit according to claim 3, wherein a content of the aromatic amine (d) in the second pack (B) is 0.01 to 5 parts by mass based on 100 parts by mass of a total of the polymerizable monomers (a1) and (a2) having no acidic group and the polymerizable monomer (b) having an acidic group that are included in the first pack and the second pack (B).

11. The polymerization initiator kit according to claim 3, wherein a content of the at least one compound (e) selected from sulfinic acid and a salt thereof in the second pack (B) is 0.01 to 20 parts by mass based on 100 parts by mass of a total of the polymerizable monomers (a1) and (a2) having no acidic group and the polymerizable monomer (b) having an acidic group that are included in the first pack (A) and the second pack (B).

12. A cured product of a mixture comprising the first pack (A) and the second pack (B) of the polymerization initiator kit according to claim 1.

13. A dental material comprising the polymerization initiator kit according to claim 1.

14. The dental material according to claim 13, wherein the dental material is one dental material selected from the group consisting of a dental adhesive resin cement, a dental composite resin, a dental backing material, a dental root filler, an orthodontic adhesive, a mobile tooth fixing material, and a dental sealant.

* * * * *